United States Patent [19]

D'Andrea et al.

[11] Patent Number: 4,765,903
[45] Date of Patent: Aug. 23, 1988

[54] PURIFICATION OF MONOMERIC INTERFERON

[75] Inventors: Mark J. D'Andrea, Neshanic Station, N.J.; Stanley J. Tarnowski, Jr., Sunnyvale, Calif.; Arthur D. Clark, Jr., Princeton, N.J.

[73] Assignee: Interferon Sciences, Inc., New Brunswick, N.J.

[21] Appl. No.: 105,629

[22] Filed: Oct. 6, 1987

[51] Int. Cl.[4] .................... B01D 15/08; C07K 15/26; A61K 45/02

[52] U.S. Cl. .................................. 210/635; 210/656; 424/85; 435/803; 435/808; 530/351; 530/413; 530/417

[58] Field of Search ................. 424/85; 530/351, 413, 530/416, 417; 435/803, 811; 210/635, 656, 659

[56] References Cited

U.S. PATENT DOCUMENTS 4,432,895 2/1984 Tarnowski ..................... 260/112 R

FOREIGN PATENT DOCUMENTS 0108585 5/1984 European Pat. Off. .

OTHER PUBLICATIONS

G. Bodo and I. Fogy, "Characterization of Different Molecular Species in Affinity Purified Recombinant Human Interferon Alpha 2," The Interferon System, pp. 23–27 (1985) (Bodo I).

G. Bodo and I. Fogy, "Molecular Species of Recombinant Human Interferon Alpha 2 Detected in Affinity Purified Preparations," TNO–ISIR Interferon System, p. 6 (1985) (Bodo II).

D. W. Bowden et al., "Cloning of Eukaryotic Genes in Single-Strand Phage Vectors: The Human Interferon Genes," Gene, 27, pp. 87–99 (1984).

J. W. Eveleigh and G. D. Winter, "Amino Acid Composition Determination," Protein Sequence Determination, Ch. 4, pp. 91–95 (1970).

A. M. Felix et al., "Analysis of Different Forms of Recombinant Human Interferons by High-Performance Liquid Chromatography," Methods in Enzymology, 119, pp. 242–248 (1986).

D. V. Goeddel et al., "The Structure of Eight District Cloned Human Leukocyte Interferon cDNAs," Nature, 290, pp. 20–26 (1981).

A. F. S. A. Habeeb, "Reaction of Protein Sulfhydryl Groups with Ellman's Reagent," Methods in Enzymology, 25, pp. 457–464 (1972).

M. W. Hunkapiller and L. E. Hood, "Analysis of Phenylthiohydantoins by Ultrasensitive Gradient High-Performance Liquid Chromatography," Methods in Enzymology, 91, pp. 486–493 (1983).

J. A. Langer and S. Pestka, "Procedure for Reduction and Reoxidation of Human Leukocyte Interferon," Methods in Enzymology, 119, pp. 248–255 (1986).

U. K. Laemmli, "Cleavage of Structural Proteins During the Assembly of the Head of Bacteriophage T4," Nature, 227, pp. 680–685 (1970).

C. R. Merril et al., "Simplified Silver Protein Dection and Image Enhancement Methods in Polyacrylamide Gels," Electrophoresis, 3, pp. 17–23 (1982).

H. Morehead et al., "Roles of the 29-138 Disulfide Bond of Subtype A of Human α Interferon in Its Antiviral Activity and Conformational Stability," Biochemistry, 23, pp. 2500–2507 (1984).

**S. Nakagawa et al., "Characterization of Three Species of Escherichia coli–Derived Human Leukocyte Interferon A Separated by Reverse-Phase High-Performance Liquid Chromatography," Journal of Interferon Research, 1, pp. 285–299 (1987).

(List continued on next page.)

Primary Examiner—Ernest G. Therkorn
Attorney, Agent, or Firm—Irene J. Frangos

[57] ABSTRACT

Fast moving monomers of alpha-2 interferon ("IFN-alpha-2") are purified from slow moving monomers and oligomers of interferon and from noninterferon proteins using a combination of immunoaffinity chromatography, reverse phase HPLC, cation exchange chromatography, and gel filtration. Two fast monomer forms, $FMM_1$ and $FMM_2$, are further distinguished on the basis of charge and hydrophobicity and $FMM_2$ is obtained in essentially homogeneous form with respect to size, hydrophobicity and charge.

10 Claims, 7 Drawing Sheets

OTHER PUBLICATIONS

I. T. Nisbet et al., "Single Amino Acid Substitutions at Conserved Residues of Human Interferon-α Can Effect Antiviral Specific Activity," *Biochemistry International*, 11, pp. 301–309 (1985).

S. Pestka et al., "Specific Immunoassay for Protein Dimers, Trimers and Higher Oligomers," *Analytical Biochemistry*, 132, pp. 328–333 (1983) (Pestka I).

S. Pestka et al., "The Specific Molecular Activities and Functional Forms of the Human Interferons," *Gene Expression*, A. B. Symp. 19, pp. 460–475 (1984) (Pestka II).

S. Pestka and S. J. Tarnowski, "Purification of the Interferons," *Pharmac. Ther.*, 29, pp. 299–319 (1985) (Pestka III).

S. Pestka et al., "Procedures for Measurement of Interferon Dimers and High Oligomers by Radio Immuno Assay," *Methods in Enzymology*, 119, pp. 588–593 (1986) (Pestka IV).

J. Porath et al., "Metal Chelate Affinity Chromatography a New Approach to Protein Fractionation," *Nature*, 258, pp. 598–599 (1975).

M. Rubinstein et al., "Human Leukocyte Interferon: Isolation and Characterization of Several Molecular Forms," *Archives of Biochemistry and Biophysics*, 210, pp. 307–318 (1981).

S. Rubinstein et al., "Convenient Assay for Interferons," *Journal of Virology*, pp. 755–758 (1981).

L. Rybacek et al., "Rapid Dual-Column Chromatographic Assay for Recombinant Leukocyte Interferon Alpha-2," *J. of Chromatography*, 397, pp. 355–364 (1987).

**S. J. Tarnowski and R. A. Liptak, Jr., "Automated Immunosorbent Purification of Interferon," *Advances in Biotechnological Processes*, 2, pp. 271–287 (1983) (Tarnowski I).

S. J. Tarnowski et al., "Large Scale Purification of Recombinant Human Leukocyte Interferons," *Methods in Enzymology*, 119, pp. 158–166 (1986) (Tarnowski II).

D. R. Thatcher and N. Panayotatos, "Purification of Recombinant Human IFN-α2," *Methods in Enzymology*, 119, pp. 166–177 (1986).

R. Uy and F. Wold, "Posttranslational Covalent Modification of Proteins," *Science*, 198, pp. 890–896 (1977).

R. Wetzel et al., "Properties of a Human Alpha-Interferon Purified from E. coli Extracts," *Journal of Interferon Research*, 1, pp. 381–390 (1981).

A. Winter et al., "Analytical Electrofocusing in Thin Layers of Polyacrylamide Gels," LKB: Application Note 250 (1977).

PANEL A: 25°C   PANEL B: 40°C

SAMPLE: LIT 1/S ELUATE
COLUMN: VYDAC C4; 5 MICRON PARTICLE SIZE; 300A PORE SIZE
DIMENSIONS: 4.6 x 250 MM
FLOW RATE: 1 ML PER MIN
TEMPERATURE: CONTROLLED BY WATERS TCM
GRADIENT PROGRAM:
  SOLVENT A: $H_2O$/0.1 % TFA
  SOLVENT B: $CH_3CN$/0.1 % TFA

| TIME | %B | CURVE |
|---|---|---|
| 0 | 5 | • |
| 5 | 5 | LINEAR |
| 15 | 45 | • |
| 45 | 45 | LINEAR |
| 50 | 100 | • |
| 55 | 100 | • |

FIG. 4

Step 2: Monoclonal Ab Column Eluate

Step 3: Reverse Phase Chromatography FMM's Fraction

Step 4: Cation Exchange Chromatography $FMM_2$ Fraction

Step 5: Purified Bulk Concentrate from Gel Filtration Chromatography

Time (min.)

Panel A:
Recombinant
Alpha 2 FMM$_2$

Panel B:
Intron A

Panel C:
Roferon A

FIG. 7

PURIFICATION OF MONOMERIC INTERFERON

This invention relates to a new method for the isolation of fully oxidized homogeneous monomeric human leukocyte interferon. More particularly, this invention relates to a method of isolating the fully oxidized form of alpha interferon through a series of purification steps including immunoaffinity chromatography, reverse phase chromatography, cation exchange chromatography and gel filtration chromatography.

BACKGROUND OF THE INVENTION

The alpha-2 subspecies of human leukocyte interferon (IFN-alpha-2) is a 165 amino acid polypeptide chain with a secondary structure characterized by two intramolecular disulfide bridges ($CYS^1$-$CYS^{98}$ and $CYS^{29}$-$CYS^{138}$) [G. Bodo and I. Fogy, "Characterization of Different Molecular Species in Affinity Purified Recombinant Human Interferon Alpha 2", *The Interferon System*, pp. 23-27 (1985); R. Wetzel, et al., "Properties of a Human Alpha-Interferon Purified From *E. coli* Extracts", *J. Interfer. Res.*, 1, pp. 381-90 (1981)]. However, in the affinity purified polypeptide, Bodo and Fogy also found species of IFN-alpha-2 in which the disulfide bonds were mispaired, or in which the critical cystines were partially or completely reduced. Certain of these forms may have a lower specific activity [See H. Moorehead et al., "Roles of the 29-138 Disulfide Bond of Subtype A of Human α Interferon in Its Antiviral Activity and Conformational Stability", *Biochemistry*, 23, pp. 2500-07 (1984)]. Alternatively, they may present a conformation which is different from the native molecule, so that an adverse reaction could be elicited upon administration. Partially or completely reduced forms are less stable and can result in further scrambled molecules.

The literature distinguishes slow-moving monomers (SMM) having at least one free sulfhydryl group (partially or fully reduced form), and a fast-moving monomer (FMM) with two disulfide bonds (fully oxidized form). The free sulfhydryl groups of SMM could give rise to oligomers through the formation of intermolecular disulfide bonds. These oligomers have a lower specific activity, and may cause adverse reactions in humans [See S. Pestka and S. J. Tarnowski, "Purification Of The Interferons", *Pharmac Ther.*, 29, pp. 299-319 (1986)]. Assays for oligomers of interferon are known [S. Pestka et al., "Specific Immunoassay for Protein Dimers, Trimers, and Higher Oligomers," *Anal. Biochem.*, 132, pp. 328-33 (1983); S. Pestka, et al., "Procedures For Measurement Of Interferon Dimers And Higher Oligomers By Radioimmunoassay", *Meth. Enzymol.*, 119, pp. 588-93 (1986)]. Considering all possible combinations of disulfide bonds and free sulfhydryl groups, theoretically ten monomeric forms of IFN-alpha-2 exist.

Upon extensive purification of the protein, D. R. Thatcher and N. Panayotatos isolated recombinant IFN-alpha-2, which they characterized as comprising a major component having a pI of 5.9 accompanied by three lesser anodic bands ["Purification of Recombinant Human IFN-α", *Meth. Enzymology*, 119, pp. 166-77 (1986)]. According to Thatcher and Panayotatos, the purification of correctly folded, fully oxidized monomer is not simple, because these "conformational variants" have properties which are very similar to those of the native molecule. Further, their work suggests that conformational variants may arise from the fact that the intracellular environment of host microorganisms has a net reducing redox potential, which favors the production of the reduced form of the monomer. Their observed conformational variants may arise from the reduced monomer.

In view of the clinical importance of pure fully oxidized form of IFN-alpha-2, attempts have been made to isolate FMM from other forms of the protein. Many procedures for the purification of IFN have been described in the literature. European patent application 108,585 refers to the removal of both oligomers and slow monomers from an interferon preparation by incubation at acid pH and elevated temperatures for a prolonged period. A. M. Felix et al., "Analysis Of Different Forms Of Recombinant Human Leukocyte Interferons by High Performance Liquid Chromatography", *Methods in Enzymology*, 119, pp. 242-48 (1986) reported the separation of SMM from FMM by a modification of the metal chelate chromatographic method of J. Porath et al. ["Metal Chelate Affinity Chromatography, A New Approach to Protein Fractionation," *Nature* (London), 258, pp. 598-99 (1975)]. U.S. Pat. No. 4,432,895 refers to the conversion of oligomeric interferon into monomeric interferon by treatment with a redox reagent. However, none has documented a method for separating fully oxidized fast moving monomers. Due to the difficulties in isolating homogeneous FMM in its native conformation in high quantities, the need for a method for its production still exists.

SUMMARY OF THE INVENTION

The present invention solves the problems referred to above by providing a means of isolating FMM in an essentially pure native form. More specifically, it provides a method for separating FMM from non-interferon proteins, oligomeric interferon, and SMM. Furthermore, our method provides for the separation of different FMM forms (i.e. $FMM_1$ and $FMM_2$) from one another.

According to this method, FMM is separated from other interferon (IFN) forms and non-interferon contaminates through various purification steps. In particular, the method involves immunoaffinity chromatography followed by reverse phase HPLC. The two forms of FMM, $FMM_1$ and $FMM_2$, cannot be separated from one another by SDS-PAGE, because they are identical in size. However, we separate them on the basis of hydrophobicity and charge, using reverse phase HPLC and cation exchange chromatography, respectively. According to this method, the $FMM_2$ can then be purified to homogeneity by gel filtration.

BRIEF DESCRIPTION OF THE DRAWINGS

FIG. 2 depicts a typical preparative RP-HPLC elution profile of the eluate from immunoaffinity chromatography (FIG. 2A); the cation exchange chromatography elution profile of the FMM fraction from RP-HPLC (FIG. 2B); a second cation exchange chromatography elution profile of the FMM fraction from RP-HPLC (FIG. 2C); and the Sephadex G-50 gel filtration elution profile of $FMM_2$ from cation exchange chromatography (FIG. 2D).

DETAILED DESCRIPTION OF THE INVENTION

The present method takes advantage of both hydrophobic and charge differences between the FMM's so that individual isomers can be completely separated to produce pure and stable fully oxidized monomers. The antibody column eluant containing recombinant IFN-alpha-2 (the product of the first step in the purification process) also contains FMM's, slow-moving monomers, fragments, dimers and higher oligomers as well as non IFN proteins. This protein mixture is bound to a reverse phase column (The Separations Group, Hesperia, Calif.) principally through hydrophobic interactions, and the proteins are chromatographed by multiple isocratic (i.e., single solvent concentration) elution steps. The fraction containing the FMM's is then bound to a cation exchange column. The cation-exchange step allows for the separation of protein molecules based on the difference of their net positive charge at a specified pH. By using an isocratic buffered salt elution, the FMM isomers are isolated. Based on the order of their elution from the cation exchange column, these isomers were named, $FMM_1$ and $FMM_2$. A size exclusion column is used as a final step to effect a buffer exchange and to separate out any residual oligomers from the monomer. The final purified $FMM_2$ is characterized as a single species on sodium dodecyl sulfate polyacrylamide gel electrophosesis (SDS-PAGE), isoelectric focusing gel electrophoresis (IEF) and analytical reverse phase high performance liquid chromatography (RP-HPLC).

The present methods may be applied to recombinant alpha- 2 interferon, as well as to natural alpha-2 interferon obtained from leukocytes, or to alpha-2 interferon prepared by organic synthesis. They may also be appropriate for obtaining monomeric forms of other alpha interferons.

In purifying either naturally derived or genetically engineered (i.e. recombinant) proteins, there is a possibility of post-translational modification of the native protein in addition to possible modification as a consequence of the purification process. These modifications may take the form of amino acid side chain chemical reactions, for example resulting in conversion of methionine to methionine sulfoxide or deamination of amino acid residues such as aspargine and glutamine. Also, the removal of end terminal (carboxy or amino) residues by exopeptidases are potential mechanisms for modification of the native protein.

The purification process herein permits, at least in the case of IFN-alpha, the recovery of the biologically active pure monomer in its native or natural state. Increased purity enhances stability, may decrease the risk of adverse reactions to contaminants, and elevates the specific activity of the resultant product.

The FMM purified according to the methods of this invention may be formulated using known procedures to prepare pharmaceutically useful compositions. Such compositions also will preferably include conventional pharmaceutically acceptable carriers and may include adjuvants, excipients or other medicinal agents. The resulting formulation will contain an amount of FMM to be effective in the intravenous, parenteral or topical treatment with IFN-alpha.

The $FMM_2$ of the present invention may be treated selectively with proteolytic enzymes or chemical reagents to obtain active fragments thereof. It may also be covalently or otherwise linked to polypeptides or other substances to create larger proteins or protein conjugates.

The FMM's purified according to the methods of this invention may be used in a variety of forms. The preferred form depends on the intended mode of administration and therapeutic application. See, for example, U.S. Pat. No. 4,680,175 (topical administration vehicle). The dosage and dose rate will depend on a variety of factors specific to the disease to be treated.

In order that this invention may be better understood, the following examples are set forth. These examples are for the purpose of illustration only and are not to be construed as limiting the scope of the invention.

EXAMPLE I

In this example we describe a process for the recovery of recombinant leukocyte (alpha) IFN $FMM_2$ from yeast cell lysate which is essentially free of yeast proteins, interferon fragments and aberrant forms of the interferon molecule.

Expression of Recombinant Alpha-2 Interferon

Recombinant DNA techniques were used to clone and express the IFN gene in yeast (*Saccharomyces cerevisiae*) using expression vector CGS 281 obtained from Collaborative Research, Inc. (Lexington, Mass.) which is deposited with the American Type Culture Collection in Rockville, Md. (ATCC No. 20663).

The feedstock to the immunoaffinity column was a cell-free clarified lysate obtained from a fermentate including yeast proteins. We obtained the clarified lysate through a multi-step procedure involving homogenization and a combination of centrifugation and tangential microfiltration. This produced a clear lysate which was then loaded onto an anti-IFN-alpha 2 monoclonal antibody-Sepharose column. The subsequent eluate contains the IFN monomers and oligomers but only a small amount of non-IFN protein contaminants (e.g., nonspecifically adsorbed yeast proteins). The purification procedure is set forth more specifically below.

Immunoaffinity Chromatography

We collected and broke open the genetically engineered yeast cells to release the recombinant IFN-alpha-2 and removed the unbroken cells and cellular debris using centrifugation and tangential microfiltration. We loaded the resultant clarified lysate onto an immunoaffinity matrix comprising an anti-IFN-alpha-2 monoclonal antibody ("LIT1") bound to Sepharose. We obtained LIT1 monoclonal antibody from Interferon Sciences, Inc. but other anti-alpha 2 interferon antibodies could be substituted [See, e.g., U.S. Pat. No. 4,423,147; European patent application 91,543; Great Britain patent 2,111,527]. We passed the lysate over our immunoaffinity matrix (hereinafter "LIT1/S") column to bind the recombinant IFN-alpha to the matrix and eliminate the majority of other lysate components and proteins. We washed the column with a phosphate buffered solution (pH 7.4) containing 1.5M NaCl and 50% (v/v) ethylene glycol. A second phosphate buffered solution (pH 7.4) containing 0.15M NaCl was used until the O.D. 280 tracing of the effluent approached zero. After the LIT1/S matrix was washed thoroughly, the bound IFN was removed by elution with an acidic buffer consisting of 0.1M citric acid, pH 2.0, containing 0.3M NaCl. An acetic acid or glycine buffer would be as effective an eluant The immunoaffinity chromatography step could be eliminated from the overall purification process if changes were made in the initial processing of the crude lysate. For example, the crude lysate could be batch adsorbed onto an appropriate reverse phase or ion exchange media. Partially purified IFN could then be removed in either a batch or column mode and the IFN further purified as indicatd below.

Reverse Phase Chromatography (RPC)

We then used RPC to separate the IFN FMMs from SMMs, dimers and higher oligomers and non-IFN-contaminating proteins. We conducted our reverse phase high performance liquid chromatography (RP-HPLC) on a Waters Binary HPLC system equipped with an automated gradient controller, two HPLC pumps, LC spectrophotometer, and a recorder/integrator. The C-4 column (22mm by 250mm; 10um particle size; 300Å pore size) was equilibrated in 0.1 (%v/v) trifluoroacetic acid (TFA) in water (HPLC grade). The IFN was bound to the reverse phase column by loading the LIT1/S eluate directly through pump A. The bound proteins were eluted from the C-4 column at a flow rate of 18 ml/min according to the following programmed gradient:

| Time | % B | Curve |
|---|---|---|
| 0 | 0 | * |
| 10 | 0 | * |
| 11 | 46 | linear |
| 41 | 46 | * |
| 45 | 100 | linear |
| 50 | 100 | * |
| 51 | 0 | linear | where solution B consists of 0.1% TFA (v/v) in acetonitrile ($CH_3CN$). The bound proteins that were subsequently eluted from the C-4 column were collected as individual fractions and the adjacent peaks corresponding to $FMM_1$ and $FMM_2$ were pooled for further purification.

Figure 1:
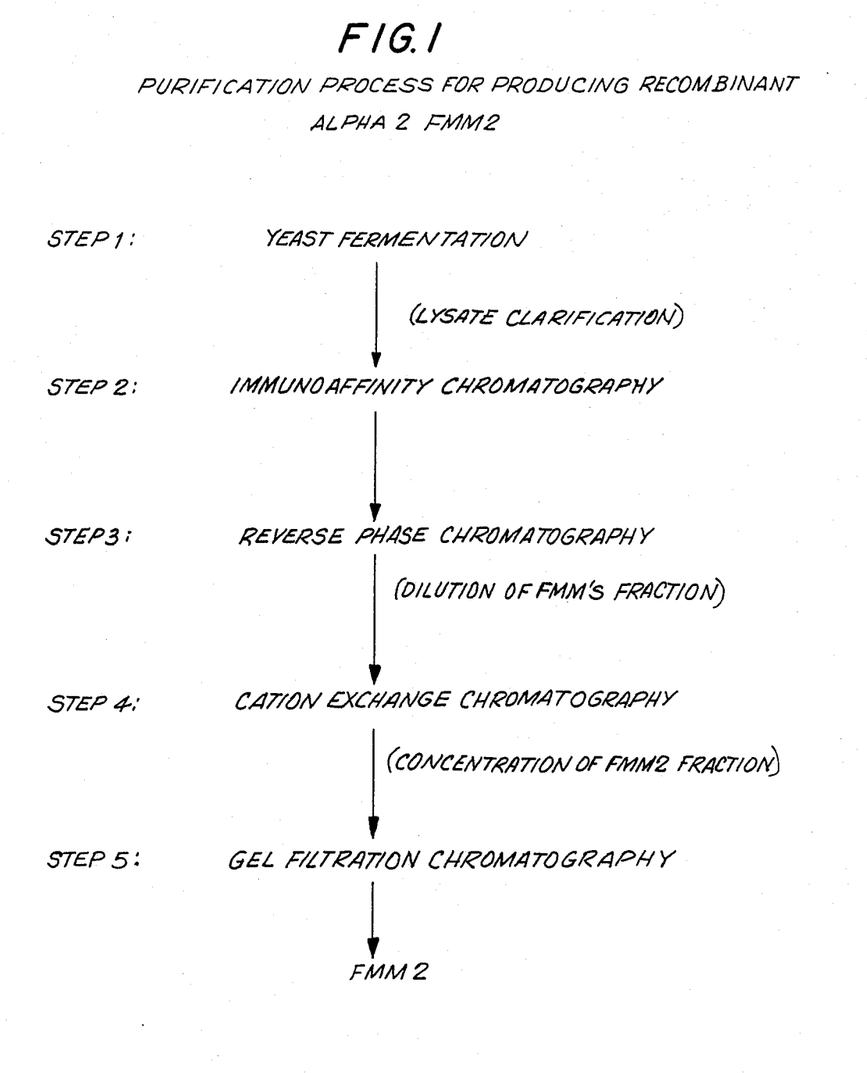
FIG. 1 outlines the purification process for producing the fully oxidized form (fast moving monomer) of recombinant alpha-2 interferon ($FMM_2$).
Figure 2A:
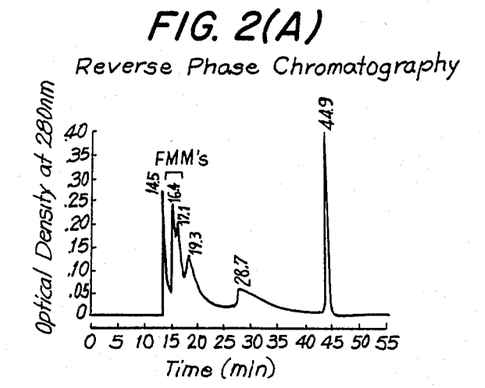

Referring now to FIG. 2A, the fractions between 15.5 min. and 18.0 min. contain the FMM's. These fractions represent a relative area percent of about 25% of the total protein load. For this particular column and operating conditions, $FMM_1$ and $FMM_2$ were eluted at about 46%B. The ratio of $FMM_1$ and $FMM_2$ was about 50:50 based on relative area percents, but this ratio can vary to 10:90 $FMM_1$:$FMM_2$. The peak eluting at 14.55 min contains non interferon proteins of yeast origin.

Optionally, hydrophobic interaction chromatography (HIC) could replace RPC, thereby obviating the use of organic solvents. Also, in scaling up the reverse phase step, a larger particle size column packing material could be used. This would permit the use of lower pressure chromatography, thereby obviating the need for expensive HPLC equipment and allowing for a more maintenance-free operation and greater ease in automating the overall system.

Further modification of the RP-HPLC step might include: use of gradient and/or isocratic solution; an increase or decrease in flow rates; organic modifiers other than acetonitrile such as n-propanol, 2-propanol, methanol, ethanol, dioxane and other substances used as eluting solvents; ion pairing agents other than TFA such as sodium dodecylsulfate, phosphoric or perchloric acids, or perchlorate salts; an increased (i.e. greater than 0.1%, v/v), or decreased amount of the ion pairing agent; use of a stationary phase with other immobilized hydrophobic groups, such as $C_3$, $C_5$, $C_8$, $C_{18}$ or phenyl; and operation at temperatures ranging from 0° C. to 56° C. A change in any one or more of the above parameters should aim toward optimizing the resolution between $FMM_2$ and other components.

We have examined the effect of varying particle size in our C-4 packings and found that the loss of resolution between the monomer species increased with increasing particle size using the elution conditions described above, but that the separation of monomer from other recombinant alpha-2 forms could still be accomplished while particle sizes were varied from 5–30 microns.

Figure 3:
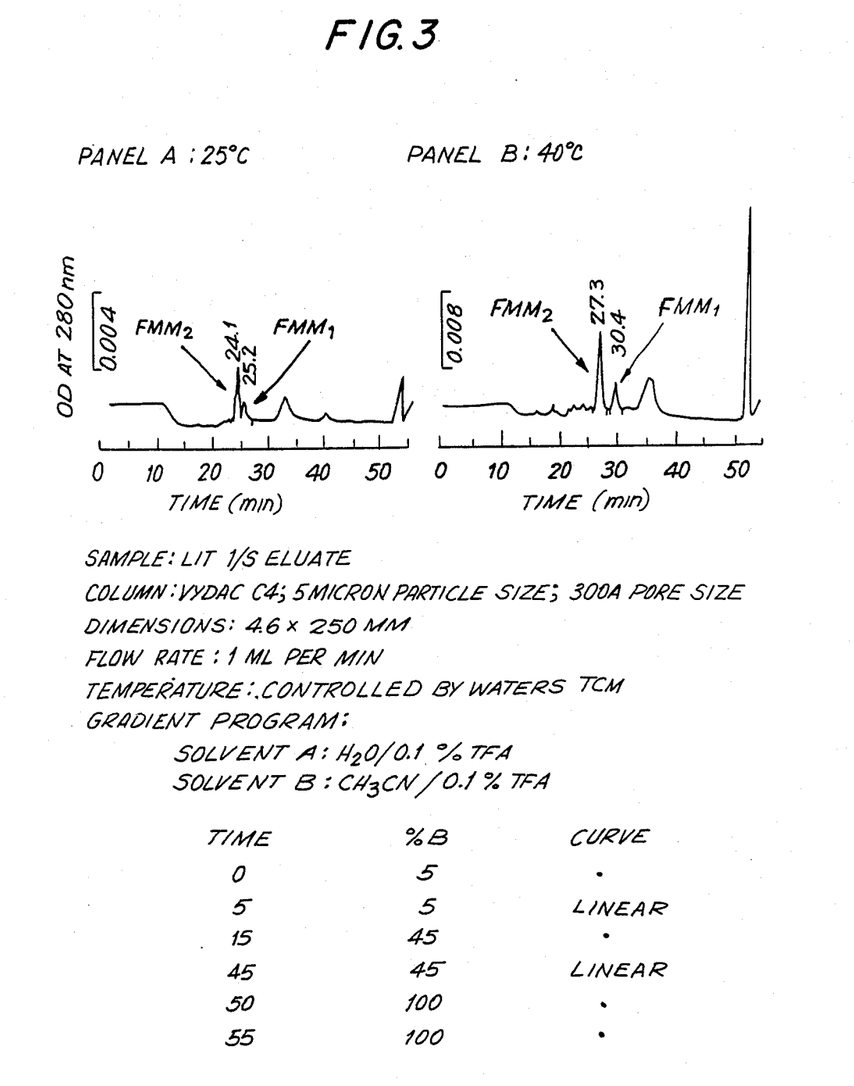
FIG. 3 depicts the improved RP-HPLC separation between $FMM_1$ and $FMM_2$ resulting from increasing the column operating temperature from 25° C. to 40° C.

$FMM_1$ and $FMM_2$ may be separated by reverse phase techniques based on the hydrophobic differences between the two species, for example, by changing the column temperature. FIG. 3 compares two chromatograms generated by controlling the column temperature at 25° C. (Panel A) and 40° C. (Panel B). The resolution between $FMM_2$ and $FMM_1$ at 40° C. is far superior (peak separation about 3 minutes) to the resolution achieved at 25° C. (peak separation about 1 minute).

We tested a S-200 gel filtration step at this stage but decided to use the C-4 column instead for several reasons: (1) large S-200 columns would be needed; (2) the sample would have to be concentrated prior to loading on the S-200 column; (3) the sample would be diluted during gel filtration; (4) the S-200 column has a limited capacity; (5) the S-200 chromatogram develops slowly (over a 24 hour period); and (6) resolution of oligomers, monomers and fragments by the S-200 column would be diminished in comparison with the separation which can be achieved with reverse phase chromatography.

Cation Exchange Chromatography

Using cation exchange chromatography we separated the $FMM_1$ and $FMM_2$ monomers based on the differences of their net positive charge at pH 5.2.

We equilibrated the cation exchange column with 0.05M ammonium acetate, pH 5.2, after exchanging the sodium counterion of the CM-Sepharose CL-6B gel with ammonium Although the acetonitrile and trifluoracetic acid from the RPC may be removed by dialysis, phase separation or lyophilization, we prefer to dilute the organic fraction containing the FMMs. The fraction was diluted approximately 8-fold with 0.05M ammonium acetate, pH 5.2 and loaded directly onto the equilibrated CM-Sepharose CL-6B column (2.54cm × 14cm) at a linear velocity of 25 cm/hr. The column was then washed with approximately two column volumes of 0.05M ammonium acetate, pH 5.2 and then eluted with 0.15M ammonium acetate, pH 5 2 at a linear velocity of 9.0 cm/hr. After we collected fractions of the resolved $FMM_1$ and $FMM_2$ monomer peaks, we eluted off strongly bound oligomers using 1.0M ammonium acetate, pH 6.0 at a linear velocity of 25 cm/hr. Although a salt gradient elution, such as 0.2M to 0.3M ammonium acetate (pH 5 0) is acceptable, we prefer to use this isocratic salt elution, particularly for large scale production.

Figure 2B:
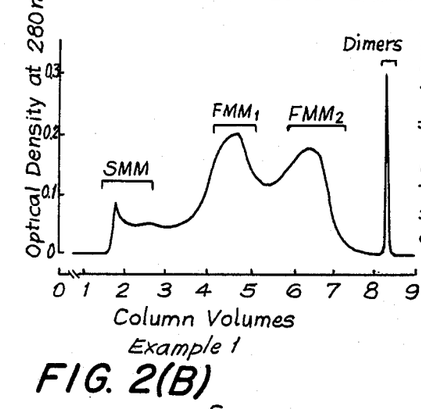

Referring now to FIG. 2B, the $FMM_1$ peak elutes between 4 and 5 column volumes, while the $FMM_2$ peak elutes between about 5.5 and 7 column volumes.

The cation exchange chromatography step could be further modified by decreasing or increasing the linear velocity; altering the eluant pH and/or ionic strength; using a buffer and counter ion other than ammonium acetate such as sodium succinate or sodium acetate; altering the column geometry; operating at higher temperatures (up to 56° C.); using gradient or isocratic elution; using an ion exchange matrix with a different ligand or ligand density, such as CM-Sepharose Fast Flow, SP-Sephadex, CM-Sephadex, CM-Trisacryl M or SP-Trisacryl M; or using a mechanically stronger support matrix than the soft gel Sepharose, such as CM-Fast Flow or CM-Silica. Any changes in the protocol presented in the example should, of course, be introduced to increase the resolution between $FMM_2$ and the other components, principally $FMM_1$.

Gel Filtration Chromatography

Figure 2C:
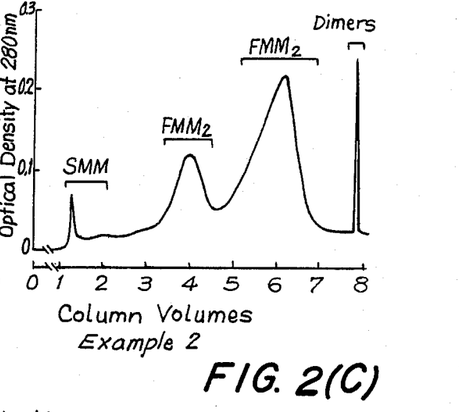
Figure 2D:
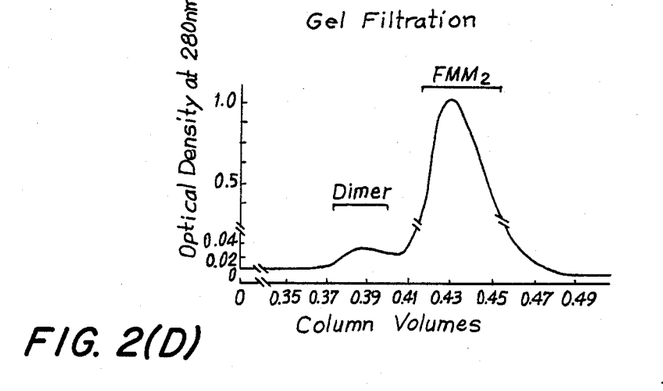

Next we concentrated the $FMM_2$ peak from the CM-Sepharose column by ultrafiltration to a protein concentration of approximately 2 mg/ml. This was loaded onto a 2.5 cm×80 cm gel filtration column (Sephadex G-50 Superfine) which had been equilibrated with 0.05M succinate buffer, pH 5.0. We then eluted at a linear velocity of 3 cm/hr using succinate buffer because it is an accepted excipient for parenteral drugs. Referring to FIG. 2D, the two resolved peaks which emerged from the column represent dimers and $FMM_2$, respectively. The $FMM_2$ peak was collected and filtered through a 0.22 um pore non-binding filter to yield a purified drug concentrate with a protein concentration of about 0.5-1.0 mg/ml in 0.05 succinate buffer, pH 5.0. We observed that the $FMM_2$ of the gel filtration eluate appeared homogeneous on a silver stained SDS-PAGE gel.

Any gel filtration column which will fractionate in the appropriate molecular weight range, such as Sephacryl S-200 Superfine, Superose-12, Fractogel 50 S Ultragel AC54 and TSK-250 gel filtration matrices, could be used in this step. In addition, ultrafiltration could replace the gel filtration step to increase the speed of the operation. However, because it is unlikely that ultrafiltration would remove any residual dimer, gel filtration is preferred. Finally, for each step, the time of operation may be decreased by increasing the flow rate.

Table I summarizes the recovery and yield per purification step for recombinant IFN-alpha-2 $FMM_2$ protein beginning with the antibody column elution. The overall percent recovery of mass is 5.8%. The recovery with respect to the $FMM_2$ content in the monoclonal antibody column eluate is 48.6%.

TABLE I

| Step | + Total Protein (mg) | % Recovery (Total) | % Recovery (Step) |
| --- | --- | --- | --- |
| Immunoaffinity chromatography | 266 | 100 | 100 |
| Reverse phase chromatography | 65 | 24.4 | 24.4 |
| Cation exchange chromatography | 20.2 | 7.6 | 31.1 |

TABLE I-continued

| Step | + Total Protein (mg) | % Recovery (Total) | % Recovery (Step) |
| --- | --- | --- | --- |
| Concentration | 17.9 | 6.7 | 88.2 |
| Gel filtration chromatography | 15.5 | 5.8 | 86.6 |

+ Estimated by optical density at 280 nm

Next, we performed a cytopathic effect assay (CPE) to determine the specific activity of our purified $FMM_2$, using the method of S. Rubenstein, et al ["Convenient Assay For Interferons," *Journal of Virology*, 37 pp. 755-58 (1981)]. First we incubated cells known to be sensitive to interferon with a serial dilution of the sample whose titer was to be determined. A challenge virus was added to each dilution. After incubating again, we observed the level of dilution which achieves a 50% reduction in viral cytopathic effect on the cells. Concentrations in terms of standard units were determined by simultaneously performing the assay on international standards, such as those established by the National Institutes of Health, Bethesda, Md.

We observed that the specific activity of $FMM_2$ was about $2.3 \times 10^8$ units/mg protein compared to about $1.0 \times 10^8$ u/mg protein for unfractioned recombinant alpha purified simply by immunoaffinity (i.e. LIT1/S) chromatography.

EXAMPLE II

In this example, the lysate "clarification" procedure was simplified, only low speed centrifugation was used; as a result, the immunoaffinity column feedstock was a cloudy lysate. We used a fluidized bed reactor for the immunoaffinity chromatography in order to process the resultant lysate. We included a three part isocratic elution program for the RPC step because the resulting LIT1/S eluate contained substantial amounts (up to 35%) of non IFN protein contaminants, such as yeast proteins. The first step essentially removes the contaminating yeast proteins; the second elutes the IFN FMMs for further purification by cation exchange chromatography; and the third removes the bulk of the IFN SMMs, oligomers and fragments.

After processing over the LIT1/S fluidized bed we recovered about 600 mg recombinant IFN-alpha-2 in the elution fraction representing about 50% of the recombinant IFN-alpha2 in the crude lysate The LIT1/S eluate (7.2 liters) was filtered over a 0.45 micron membrane and loaded onto a preparative Vydac C-4 (22 mm×250 mm) reverse phase column in eight portions. Each load was eluted with a multi-step isocratic gradient of acetonitrile as shown below:

| Time (min.) | % B | Curve |
| --- | --- | --- |
| 0 | 0 | * |
| 10 | 0 | * |
| 11 | 43 | linear |
| 20 | 43 | * |
| 21 | 46 | linear |
| 36 | 46 | * |
| 40 | 100 | linear |
| 45 | 100 | * |

The FMM fraction representing the elution from about 24.5 to 26.0 minutes from each run was pooled. We recovered 105 mg of FMM from the LIT1/S column eluate, representing 92% of the theoretical yield of 115 mg, as determined by analytical RP-HPLC.

The FMM fraction was diluted to 6% (v/v) acetonitrile with 0.05M ammonium acetate, pH 5.2 and loaded onto a 200 ml (4.4×14 cm) cation exchange column (CM-Sepharose CL-6B). The column was eluted isocratically with 0.14 M ammonium acetate, pH 5.2. Our results are depicted in FIG. 2C. The slight decrease in the molarity of the ammonium acetate buffer (0.15M to 0.14M) improved the resolution between $FMM_1$ and $FMM_2$ over previous separations (see Example I). We combined fractions representing the $FMM_2$ peak and concentrated them to about 5 mg protein/ml using ultrafiltration. The concentrated $FMM_2$ was loaded onto a Sephadex G-50 Superfine gel filtration column to remove trace oligomers and exchange ammonium acetate for 0.05M succinate buffer (pH 5.0). The protein concentration of the $FMM_2$ eluate from the gel filtration column was about 1 mg/ml and had a specific activity of about $2.2 \times 10^8$ units/mg protein. Table II summarizes the recovery and yield per purification step for $FMM_2$. The overall recovery based on protein mass was 7.3% from the total protein and about 50% relative to the total $FMM_2$ contained in the LIT1/S column eluate.

TABLE II

| Step | +Total Protein (mg) | % Recovery (Total) | % Recovery (Step) | Sp. Act. ($\times 10^{-6}$ u/mg) |
|---|---|---|---|---|
| LIT1 monoclonal antibody | 600 | 100 | 100 | 116 |
| Reverse phase chromatography | 105 | 14.4 | 17.5 | 168 |
| Cation exchange chromatography | 49.4 | 8.2 | 47.0 | 149 |
| Gel filtration chromatography | 43.5 | 7.3 | 88.1 | 210 |

+ Estimated by optical density at 280 nm

Figure 4:
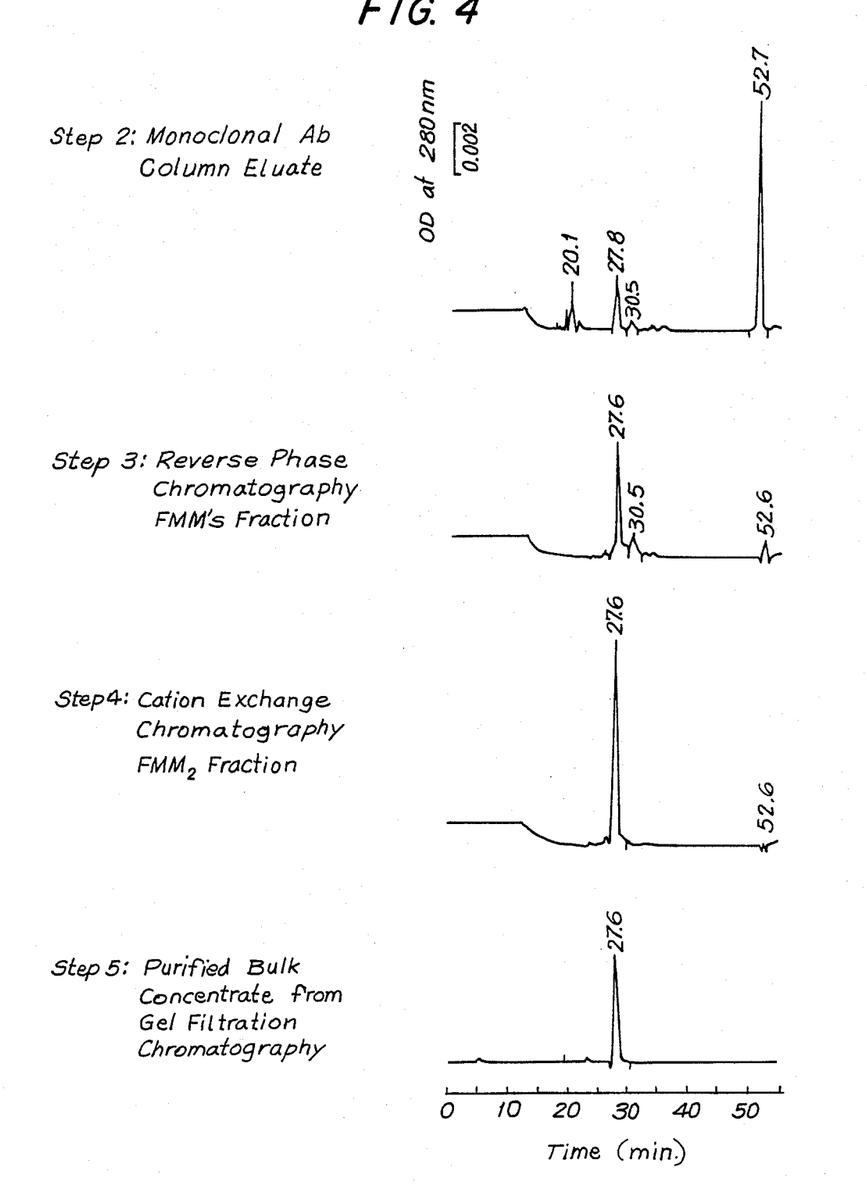
FIG. 4 presents the RP-HPLC analysis of the recombinant IFN-alpha-2 $FMM_2$ purification intermediates.

FIG. 4 depicts a comparison of analytical RP-HPLC profiles for each intermediate of the purification process and confirms the homogeneity of the $FMM_2$ final purified drug concentrate.

EXAMPLE III

Characterization of $FMM_1$ and $FMM_2$

We prepared samples of $FMM_2$ for characterization as described above. To prepare the $FMM_1$, we further purified our samples by rechromatographing the cation exchange $FMM_1$ fraction on RP-HPLC and collecting the peak corresponding to $FMM_1$ to remove any residual $FMM_2$ or SMM. In side-by-side analysis, the specific activity of $FMM_1$ was found to be about the same as that for $FMM_2$ (about $200 \times 10^6$ u/mg).

A. Isoelectric Focusing Gel Electroohoresis (IEF)

We analyzed samples using a modification of the technique described by A. Winter ["Analytical Electrofocusing in Thin Layers of Polyacrylamide Gels" LKB Application Note 250 (1977)]. Samples were diafiltered against 5 mM Tris-HCL, pH 8.0, and concentrated in an Amicon Centricon ™ unit equipped with a 10,000 MWCO membrane. Electrofocusing was performed with LKB (Bromma, Sweden) analytical electrofocusing equipment using horizontal precasted LKB Ampholine ® PAG plates (pH 3.5 to 9.5). Prior to the application of about 10 ul of each sample (approximately 5-10 ug protein) the gel was prefocused for 0.5 hours at 50 watts of constant power. The electrophoresis was performed for 1-2 hours with cooling or until constant current was achieved. We obtained the isoelectric point markers from Pharmacia Fine Chemical, Inc. (Piscataway, NJ). The gel was fixed overnight at room temperature in a 30% methanol, 3.5% sulfosalicylic acid, 11.5% trichloracetic acid solution. The gel was then stained at 60° C. for 10 min. using 0.1% (w/v) Coomassie brilliant blue R-250 in 8% acetic acid in 25% methanol. Finally, the gel was destained to a clear background by diffusion in a solution of 8% acetic acid in 25% methanol.

The results of our IEF gel electrophoresis revealed that $FMM_1$ had a pI of about 5.85, while that of $FMM_2$ was about 6.06.

We do not believe that the difference in isoelectric points between $FMM_1$ and $FMM_2$ is attributable to methionine sulfoxide residues, because the peptide maps of the cyanogen bromide digests from the two monomers were indistinguishable.

B. Sodium Dodecyl Sulfate Polyacrylamide Gel Electrophoresis (SDS-PAGE)

We analyzed our samples in 5 mM Tris-HCL, pH 8.3 according to the method of U. K. Laemmli ["Cleavage of Structural Proteins During the Assembly of the Head of Bacteriophage T4," Nature (London), 227, pp. 680-85 (1970)]. We mixed a volume of the concentrate, comprising 5 to 10 ug protein, with a volume of sample buffer, to yield a final concentration of 0.1% SDS (w/v) 10% glycerol (v/v) in 10 mM Tris-HCL, pH 6.8. The samples were then heated to 95° C. for three minutes. When reduced samples were required, 2-mercaptoethanol was added to the samples to a final concentration of 10% (v/v). We applied the samples to preformed wells in a 4% polyacrylamide stacking gel (1.0×18×0.75 cm) and electrophoresed them over a 14.5% polyacrylamide resolving gel (16×18×0.75 cm) each containing 0.1% (w/v) SDS. We performed the electrophoresis at 30 milliamps constant current, with cooling, until the tracking dye front (bromophenol blue) migrated to the bottom of the gel (approximately 3 hours). The gel was fixed and stained for about 1 hour at room temperature with 0.1% (w/v) Coomassie brilliant blue R-250 in isopropanol/acetic acid/water (25:10:65), and destained to a clear background by diffusion with methanol/acetic acid/water (5:10:85). When it was necessary to increase the sensitivity of the staining process, or when the protein loaded onto the gel was below the limit of detection by Coomassie blue staining, the gels were stained with a 0.012 M silver nitrate ($AgNO_3$) solution according to the procedure of C. Merril et al. ["Simplified Protein Detection and Image Enhancement Methods in Polyacrylamide Gels," Electrophoresis, 3, pp. 17-23 (1982)]. Using SDS-PAGE analysis, we found $FMM_1$ and $FMM_2$ to be indistinguishable under both nonreducing and reducing conditions. Under nonreducing conditions, both migrated with an apparent molecular weight of about 19,000 daltons.

C. Amino Acid Composition

We determined the concentration of amino acid residues using hydrochloric acid to hydrolyze between 0.5 to 1.0 nanomole of sample at standard conditions of about 100° C. for 24 hours according to the procedure of J. W. Eveleigh ard G. D. Winter ["Amino Acid Composition Determination", Protein Sequence Determination, pp. 91-95 (1970)]. For the determination of MET and CYS concentrations, performic acid hydrolysis was performed. We analyzed the amino acids of the resulting hydrolysate using a Durram Model D-500 amino acid analyzer with ninhydrin and fluorescence for detection.

A total of 8 samples each of $FMM_2$ and $FMM_1$ were analyzed. The mean and standard deviation are presented in Table III. Our results indicate that there is no significant difference between $FMM_1$ and $FMM_2$ based on amino acid composition.

TABLE III

| Residue | Amino Acid Analysis (± standard deviation) | | |
|---|---|---|---|
| | FMM1 | FMM2 | Predicted* |
| ASX | 13.91 (±1.05) | 14.22 (±1.20) | 12 |
| THR | 10 | 10 | 10 |
| GLY | 7.44 (±1.10) | 8.02 (±1.87) | 5 |
| ALA | 8.86 (±0.53) | 8.91 (±0.69) | 8 |
| VAL | 6.61 (±0.36) | 6.40 (±0.21) | 7 |
| HIS | 2.93 (±0.53) | 3.05 (±0.63) | 3 |
| ARG | 10.47 (±0.82) | 10.66 (±0.95) | 10 |
| TYR | 5.20 (±0.09) | 5.17 (±0.16) | 5 |
| PHE | 9.51 (±1.37) | 9.67 (±1.09) | 10 |
| SER | 13.89 (±0.55) | 14.15 (±0.50) | 14 |
| GLX | 28.06 (±0.82) | 28.16 (±1.07) | 26 |
| ILE | 7.39 (±0.61) | 7.48 (±0.68) | 8 |
| LEU | 20.47 (±1.83) | 20.76 (±2.46) | 21 |
| LYS | 9.97 (±0.89) | 10.04 (±1.20) | 10 |
| PRO | 4.99 (±0.54) | 4.46 (±1.26) | 5 |
| CYS | 4.00 (±0.85) | 3.85 (±0.49) | 4 |
| MET | 5.35 (±0.35) | 5.35 (±0.21) | 5 |
| TRP | 2** | 2** | 2 |
| | | | 165 |

*As determined from the cDNA nucleotide sequence of the cloned IFN alpha 2 gene and the putative amino acid sequence.
**Determined by IBA (iodosobenzoic acid) cleavage and mapping essentially according to the procedure by A. Fontana, Biochemistry, 20, pp. 6997-7004 (1981).

D. N-Terminal Sequencing of $FMM_1$ and $FMM_2$

About 0.5 to 1.0 nanomole of an S-carboxy methylated sample was dissolved in TFA and sequenced on an 470A gas phase sequencer (Applied Biosystems) using current automated Edman degradation methodology [M.W. Hunkapiller and L. E. Hood, "Analysis of Phenylthiohydantoins by Ultrasensitive Gradient High Performance Liquid Chromatography", *Methods in Enzvmolooy*, 91, pp. 486–93 (1983)]. The PTH-amino acids were analyzed by RP-HPLC on a Waters Model 6000 gradient system with WISP autosampler and a fixed wavelength detector. We analyzed our data using Nelson Analytical Software and an IBM computer.

$FMM_2$ Results:

```
        5                              10
CM.CYS—ASP—LEU—PRO—GLN—(THR)—HIS—SER—LEU—GLY 15                           20
SER—ARG—ARG—(THR)—LEU—MET—LEU—LEU—ALA—GLN 22   23
MET—ARG—ARG—ILE
```

The N-terminal sequence for $FMM_2$ corresponds exactly to that published for the mature recombinant alfa-2 IFN [D. V. Goeddel, et al., "The Structure of Eight Distinct Clone Human Leukocyte Interferon cDNAs", *Nature*, 290, pp. 20–26 (1981)] except for position 23 where Goeddel predicts a LYS. The amino acid residues enclosed in parentheses represent uncertainty in our analysis.

$FMM_1$ Results

We were unable to obtain sequence data using the normal Edman degradation procedure. We concluded, therefore, that the protein is blocked at its N-terminus.

E. Determination of Sulfhydryl Groups

We measured sulfhydryl groups in a pure preparation of $FMM_1$ and $FMM_2$ using Ellman's reagent, 5,5'-dithio-bis-(2-nitrobenzoic acid) (DTNB) using a modification of Habeeb's procedure [A.F.S.A. Habeeb, "Reaction of Protein Sulfhydryl Groups with Ellman's Reagent," *Methods in Enzymology*. 25, pp. 457–64 (1972)]. We gently mixed 666 ul of a 6M Gu-HCl solution (pH 8.3) containing 20 mM EDTA, about 10 nanomoles of sample protein in 327 ul of 0.5 M Tris-HCl (pH 8.3, 20 mM EDTA), and 90 ul of 10 mM DTNB in water at room temperature for 30 minutes. We measured the absorbance at 412 nm using freshly prepared cysteine solution (2mM) in 20 mM EDTA (pH 8.3) as a standard. The molar extinction coefficient under these conditions ranged from 13,000 to 13,600, which agreed well with the reported value.

Our results for both $FMM_1$ and $FMM_2$ indicated less than 0.1 moles of SH per mole of protein, representing that both our $FMM_1$ and $FMM_2$ are fully oxidized.

F. Analytical Reverse Phase High Performance Liquid Chromatography (RP-HPLC)

RP-HPLC was performed on a (Waters) Binary HPLC System equipped with an automated data controller Model 680, two Model 510 pumps, an LC spectrophotometer Model 481, a Rheodyne injector, a Waters column temperature control module and a Shimatzu recorder/integrator.

We analyzed samples of at least 20 ug with a Vydac C-4 reverse phase column (4.6 mm×25 cm; 5 um particle size) maintained at a constant temperature of 40° C. The column was equilibrated in 0.1% (v/v) trifluoroacetic acid (TFA) in water. We developed a gradient elution at 1 ml/min flow rate with acetonitrile ($CH_3CN$) in 0.1% (v/v) TFA (Solvent B) according to the following program:

| Time | % B | Curve |
|---|---|---|
| 0 | 5 | * |
| 5 | 5 | * |
| 15 | 45 | Linear |
| 45 | 45 | * |
| 50 | 100 | Linear |
| 55 | 100 | * |

We monitored the column effluent for absorbence at 280 nm.

Under these chromatographic conditions, we observed that $FMM_2$ and $FMM_1$ each migrates essentially as a single symmetrical peak at a retention of 27.6 minutes (see FIG. 4, step 5) and 30.4 minutes (data not shown), respectively.

G. Tryptic Mapping of FMM1 and FMM2

We purified TPCK-treated trypsin according to the method of Rovery [*Methods in Enzymology, vol. XI*, pp. 231–39 (1967)]. About two nanomoles of a 5-carboxamidomethylated sample was digested two times with a 1:75 weight ratio of the purified trypsin to protein ($FMM_1$ or $FMM_2$). The digestion was carried out in 0.1M $NH_4HCO_3$, pH 8.0, for 2 hours at 37° C. After digestion, the pH of the peptide mixture was adjusted to 2.0 with 2% TFA in water. The peptide mixture was dried and twice redissolved in 0.1% TFA in water and dried again. Finally, the peptide mixture was taken up in a known volume of 0.1% aqueous TFA.

We generated tryptic maps using RP-HPLC. We loaded about 2 nanomoles of each digest separately onto a reverse phase column (Vydac C-18, 5 micron particle size, 300Å pore size, 4.6 mm×250 mm) equilibrated at 95% water, 5% acetonitrile (0.1% TFA). The peptides were eluted at 30° C. with a linear gradient of 0.23% acetonitrile per minute from 5–50% acetonitrile. Peaks were monitored at 215 nm.

Figure 7:
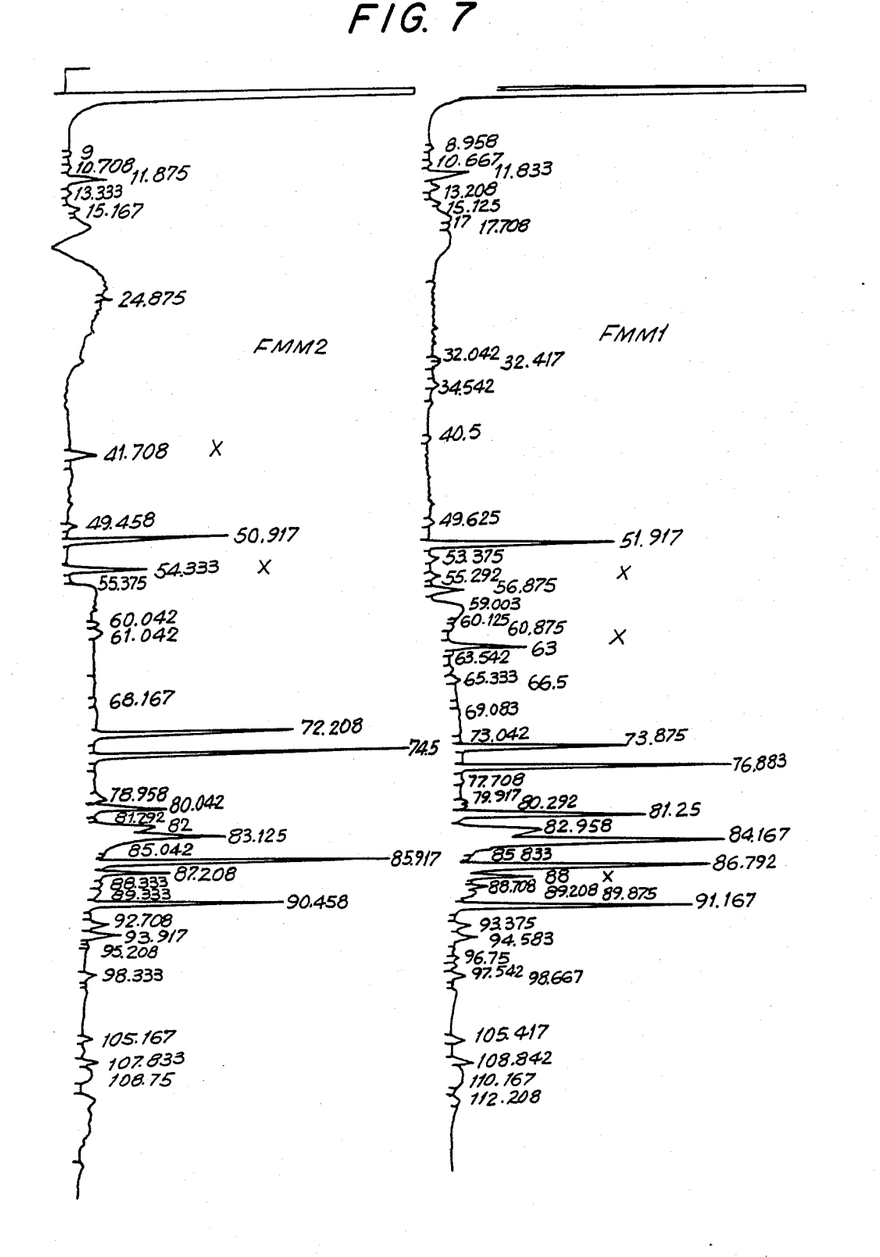
FIG. 7 depicts the tryptic mapping of $FMM_1$ and $FMM_2$.

As controls, we ran: (a) trypsin alone, using the same conditions as those used for the peptide mixture; (b) nondigested $FMM_1$ or $FMM_2$; and (c) alkylated, nondigested $FMM_1$ or $FMM_2$. The control runs were found not to interfere with the peptide maps as presented in FIG. 7. We observed distinct differences between the $FMM_1$ and $FMM_2$ monomers (see FIG. 7).

EXAMPLE IV

Comparison of Recombinant alpha 2 $FMM_2$ with Intron ® A(Schering-Plough) and Roferon ® A (Hoffman LaRoche)

We obtained Intron A and Roferon A from a local pharmacy and analyzed the respective interferon compositions. This was accomplished by using a rapid assay for determining recombinant leukocyte interferon alpha-2 in complex mixtures. The assay relies on the use of a high performance monoclonal antibody affinity column connected in tandem with a reverse phase HPLC column [L. Rybacek et al., "Rapid Dual-Column Chromatographic Assay For Recombinant Leukocyte Interferon Alpha-2", *J. Chromatography.*, 397, pp. 355–64, (1987)].

Figure 5:
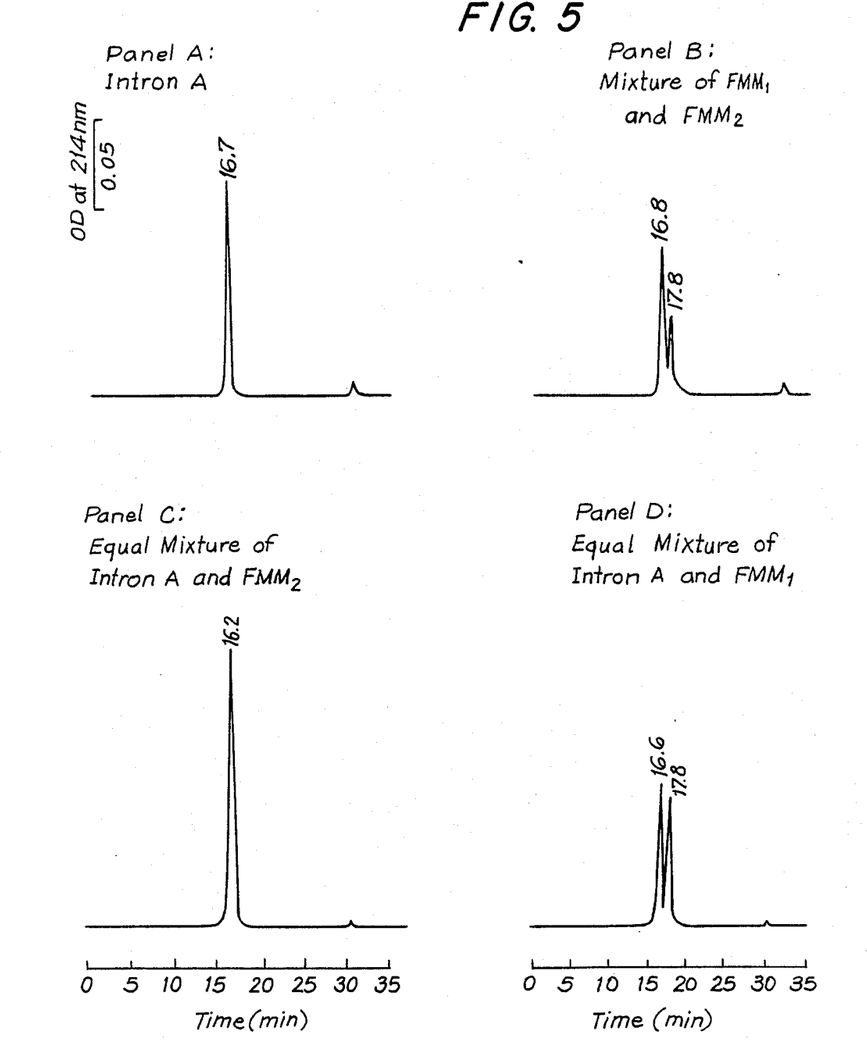
FIG. 5 presents a RP-HPLC comparison of recombinant IFN-alpha-2 $FMM_1$ and $FMM_2$ with Intron ® A.

After collection of the interferon from the rapid assay system, we loaded either the HSA-free Intron A or Roferon A onto an analytical Vydac C-4 column (4.6 mm×250 mm; 5 micron particles size) and developed the chromatogram with a step gradient to 44% acetonitrile in 0.1% trifluoroacetic acid at 1 ml/min. Referring to FIG. 5A, we observed that Intron A elutes as one peak with a retention time of 16.7 min. A mixture of recombinant IFN-alpha-2 $FMM_1$ and $FMM_2$ was then chromatographed under identical conditions. The $FMM_2$ eluted at a retention time near Intron A (16.8 min.) whereas $FMM_1$ eluted one minute later at 17.8 min (FIG. 5B). In a further study, we subjected mixtures of equal amounts of Intron A and recombinant IFN-alpha-2 $FMM_1$ and equal amounts of Intron A and recombinant IFN-alpha-2 $FMM_2$ to the reversephase chromatography as described above. Referring to FIG. 5C, $FMM_2$ and Intron A were found to coelute from the reversephase column, while $FMM_1$ and Intron A showed unique retention times (FIG. 5D).

Figure 6:
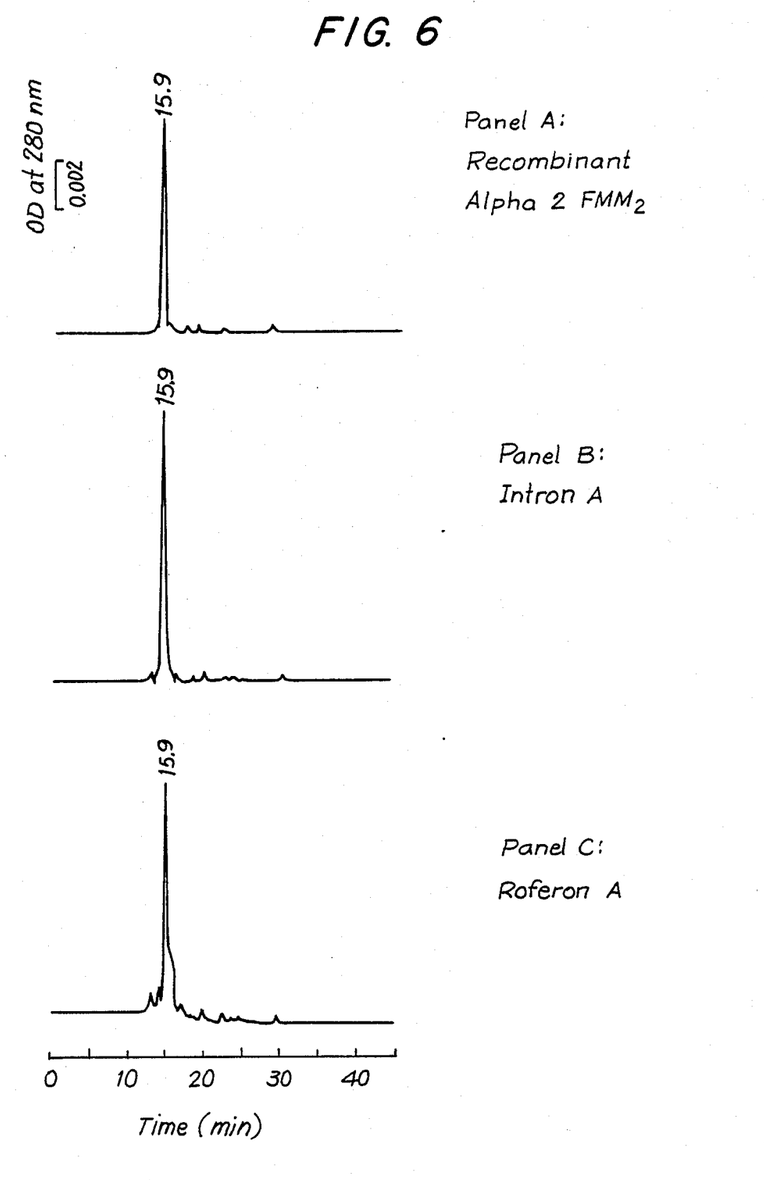
FIG. 6 presents a RP-HPLC comparison of recombinant IFN-alpha-2 $FMM_2$ with Intron ® A and Roferon ® A.

In a separate experiment, the reverse-phase chromatograms for Roferon A, Intron A and recombinant IFN-alpha-2 $FMM_2$ were compared. Referring to FIG. 6, the main peaks in each sample had closely corresponding retention times, but the Roferon A (FIG. 6C) contained a trailing shoulder on the main peak. These results suggest that Roferon A is more heterogeneous or that it contains more degradation products than either recombinant alpha 2 $FMM_2$ (Panel A) or Intron A (Panel B).

We also compared recombinant IFN-alpha-2 $FMM_2$ to Intron A and Roferon A using isoelectric focusing gel electrophoresis. Our results indicated that recombinant IFN-alpha-2 $FMM_2$ had the fewest isoelectric species. Intron A showed at least two isoelectric forms and Roferon A had at least four, while our $FMM_2$ showed only one form. Also, the major band in Roferon A had an isoelectric point that is distinct from $FMM_2$ and Intron A. This difference may be attributed to the primary structural difference between alpha 2 and alpha A, which is an arginine to lysine substitution at position 23 of the polypeptide chain.

In another study, we compared $FMM_2$ to Intron A and Roferon A after SDS-polyacrylamide gel electrophoresis under both non-reducing and reducing conditions. Our results indicated that the products were indistinguishable with respect to size, except that Intron A contained a trace amount of dimers, and Roferon A contained some unidentified high molecular weight proteins.

EXAMPLE V

Stability of Recombinant-IFN Alpha 2 $FMM_2$ Purified Concentrate

Recombinant IFN-alpha-2 $FMM_2$ purified concentrate (SpA $2.3 \times 10^8$ U/mg) was stored at 0.48 mg/ml in 0.05M succinate buffer, pH 5.0, at several temperatures ($-20°$ C., 4° C., 25° C. and 37° C.) for four weeks. We evaluated each temperature point for activity with the CPE assay and degradation with SDS-PAGE. Even after four weeks at 37° C., the specific activity was unchanged (averaging approximately $2.5 \times 10^5$ u/mg) Additionally, after seven weeks at 37° C., analysis of $FMM_2$ by SDS-PAGE on a silver stained gel failed to reveal any oligomers or degradative low molecular weight products in the non-reduced sample, and there was a trace of low molecular weight material in the reduced sample.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A method of isolating the fully oxidized form of human alpha-2 interferon fast moving monomer (FMM), essentially free of partially or fully reduced forms of slow moving monomers (SMM) and oligomers of leukocyte interferon and of non-interferon proteins comprising:
   (a) loading unpurified human alpha-2 interferon ("IFN-alpha-2") sample containing the fully oxidized form of human alpha-2 interferon fast moving monomer on a lower alkyl reverse phase column, and eluting;

(b) loading the product of step (a) on a cation exchange column and eluting;

(c) loading the product of step (b) on a gel filtration column and eluting; and (d) recovering said fast moving monomer in purified form.

2. The method of claim 1, wherein the IFN-alpha-2 is first purified by immunoaffinity chromatography.

3. The method of claim 2, wherein IFN-alpha-2 is eluted from the immunoaffinity column by an acidic buffer.

4. The method of claim 1, wherein the reverse phase column is a C-4 column and the FMM is eluted at about 0.1% trifluoracetic acid and about 46% $CH_3CN$.

5. The method of claim 1, wherein the cation-exchange column is an immobilized carboxymethyl column.

6. The method of claim 1, wherein the FMM is collected from the gel filtration column beginning at about 0.45 fraction of the total column volume.

7. The method of claim 1 in which the reverse phase chromatography of step (a) is on a C-4 column, the ion exchange chromatography of step (b) is on a carboxymethylated column, the eluting agent in Step (a) is trifluoracetic acid in acetonitrile, and the eluting agent of step (b) is ammonium acetate.

8. The method of claim 1 wherein the elution of step (a) is carried out under isocratic conditions.

9. The method of claim 1, wherein different FMMs of alpha-2 interferon are separated on the basis of charge and hydrophobicity.

10. The method of claim 9, wherein the separated monomers are $FMM_1$ and $FMM_2$.

* * * * *